(12) United States Patent
Ladron de Guevara et al.

(10) Patent No.: US 8,580,121 B2
(45) Date of Patent: Nov. 12, 2013

(54) METHOD FOR MONITORING AND CONTROLLING A PROCESS FOR TREATMENT OF A TREATABLE FLUID

(76) Inventors: Cesar Ladron de Guevara, Las Vegas, NV (US); Leonard Davidson, Henderson, NV (US)

(*) Notice: Subject to any disclaimer, the term of this patent is extended or adjusted under 35 U.S.C. 154(b) by 233 days.

(21) Appl. No.: 12/655,534

(22) Filed: Dec. 31, 2009

(65) Prior Publication Data
US 2011/0155255 A1    Jun. 30, 2011

(51) Int. Cl.
*B01D 21/30* (2006.01)
(52) U.S. Cl.
USPC ............ 210/709; 210/739; 210/745; 210/746
(58) Field of Classification Search
USPC ........................................................ 210/709
See application file for complete search history.

(56) References Cited

U.S. PATENT DOCUMENTS

| | | | | |
|---|---|---|---|---|
| 4,855,061 A | * | 8/1989 | Martin | 210/709 |
| 5,045,213 A | * | 9/1991 | Bowers | 210/709 |
| 5,869,342 A | * | 2/1999 | Stannard et al. | 436/55 |
| 6,346,198 B1 | * | 2/2002 | Watson et al. | 210/739 |
| 2006/0289358 A1 | * | 12/2006 | Milchuck | 210/702 |

* cited by examiner

*Primary Examiner* — Tony G Soohoo
*Assistant Examiner* — Peter Keyworth
(74) *Attorney, Agent, or Firm* — Holtz, Holtz, Goodman & Chick, PC

(57) ABSTRACT

The present invention relates to a means of monitoring and controlling a process step, or steps for a treatable fluid being processed, whereby a sampled volume of the treated fluid is delivered to a vessel, within which the sampled treated fluid emulates the expected reaction or reactions of the treatable fluid being processed within the process step. The sampled volume of the treated fluid is detained, monitored, recorded and analyzed by the present invention. The resulting data is translated into commands that are conveyed to process control devices which control the processing of the treatable fluid. Sampling and analyzing of the treatable fluid is automatically repeated on a cyclical basis.

17 Claims, 2 Drawing Sheets

METHOD FOR MONITORING AND CONTROLLING A PROCESS FOR TREATMENT OF A TREATABLE FLUID

FIELD OF THE INVENTION

The following invention relates to fluid control systems which are configured to control the introduction of a treatment fluid into a fluid stream to cause a selected characteristic of the fluid stream to match a desired level. More particularly, this invention relates to treatment fluid injection control systems which divert sampled fluid stream solutions, sampled from the fluid stream after its treatment fluid injection point, which detain the sampled fluid stream solution, which analyze the detained sampled fluid stream solution and which use the results of this analysis to control a main treatment fluid flow rate into the fluid stream.

BACKGROUND OF THE INVENTION

Many types of fluid handling systems require monitoring of selected characteristics of the fluid stream to control the introduction of treatment fluids into the fluid stream. For instance, in water and wastewater treatment facilities a main stream of contaminated water typically is treated with a flocculating agent, such as ferric chloride and chemical polymers, to facilitate flocculation and precipitation of unwanted particulates such as suspended and dissolved solids contained within the water stream. It is undesirable to under treat the water stream because excessive amounts of unwanted particulates will thus remain in the water stream. It is also undesirable to over treat the water with flocculating agents because any excess quantity of flocculating agent other than that which is required to perform the process of flocculation and precipitation is wasteful, costly and provides no additional benefit.

Many advanced water treatment systems include a turbidity sensor and analyzer downstream from the vessel that within which the processes of flocculation and precipitation occur. The turbidity sensor is used to monitor the residual particulates in the water stream. Controllers which utilize the results of this downstream analyzer are known to provide a feedback signal to the chemical feed pump. In essence, if an amount of turbidity is too high at the downstream analyzer, the chemical feed pump receives a feedback signal which increases the rate of introduction of flocculating agent. If the analyzer detects that lesser turbidity exists than that which is pre-determined to be below the acceptable turbidity set point range, the chemical feed pump receives a feed back signal from the controller decrease the rate of introduction of flocculating agent.

While such turbidity analyzers and feedback control systems are generally effective, they suffer from numerous drawbacks. For instance, when the analyzer detects a less than optimal amount of flocculating agent has been utilized indicated by way of a high turbidity result as read by the analyzer, additional treatment must still be provided to the water stream in order to properly treat the water. The delay in responding to a change in the desired process results is associated with the process flow volume contained within the distance between the analyzer's sensor location and the chemical feed pump injection point and the amount of time it takes for the flow to reach the sensor from the chemical feed injection point. The delay for the turbidity analyzer to detect and react to any change required in the chemical feed rate in order to compensate for the detected change in the resulting process characteristic causes an in-efficient utilization of the injected chemical. The wasteful amount of chemical usage can be directly associated with the chemical feed rate multiplied by the time it takes for the flow to travel from the injection point to the sensor multiplied by the differential of chemical fluid flow required to meet the set point objective and the amount of fluid being delivered. It should also be noted that the volume of improperly treated processed flow that is ultimately discharged form the process is associated with the process flow rate multiplied by the time for the flow to travel from the injection point to the sensor. As is described in such an example, in the results derived from the delay in reacting to a flocculating and precipitating process can causes problems in the its control. Such is with traditional feedback systems because they have a tendency to enter into an oscillatory state between over and under turbidity set point ranges which only relatively slowly resolves itself, especially when the chemical requirement and the particulates within the water stream is fluctuating. Water treatment facilities can incur higher chemical usage, higher plant operational costs and possible fines for releasing water which is under treated or over treated with flocculating agents. Water treatment facilities additionally suffer financially from the unnecessary excessive use or insufficient use of flocculating agents such as synthetic polymeric flocculants and ferric chloride. Additionally, if the flocculating and precipitating process is not properly regulated, the resulting effluent quality from this process step has a determining factor for the efficiencies and operational costs associated with further treatment steps that might be utilized in the overall processing of the water flow. These further processing steps of the water flow might include filtration, polishing and disinfection.

Other fluid control systems exhibit a need corresponding to that identified above. Specifically, systems which require treatment of a main fluid stream injected with a treatment fluid to cause a selected characteristic of the main fluid stream to match a desired level/set point or range often cannot be effectively controlled by having a sensor downstream from the treatment fluid injection site at the effluent discharge conduit of the process equipment, that which through its analyzer, feeds back a signal to the treatment fluid injection controller.

Other analyzer technologies exist that utilize sampler chambers as a part of their sensing and data collection systems. These data collection systems for monitoring and reporting fluid characteristics, as is represented by the Hach Company's 1720E Low Range Turbidity Analyzer, uses a sampler chamber as a recipient of the treated stream flow to be measured by its turbidity sensor. Its specially designed sampler chamber is utilized to receive a constant flow from either the pre-treated fluid stream flow or the process effluent stream flow. The purpose of utilizing this sampler chamber is to provide for a means of the removal of bubbles and grit within a controlled low flow rate environment of its sampler chamber and thus obtaining a more precise reading of the fluid characteristic by its sensor than would traditionally be obtained in a fluid characteristic reading from within the more turbulent environment of the main flow stream. These technology types, such as the Hach 1720E system, are utilized when meeting compliance and reporting standards of the U.S. Environmental Protection Agency regulation, specifically USEPA 180.1 are an issue.

The present invention differs with technology types as mentioned prior in that the present invention is a combination chemical process results analyzer and chemical process controller, and its use of a sampler chamber provides for a chamber within which the treated fluid sample is detained, and wherein the treated sampled fluid is permitted to react so as to emulate the process step of the main treated fluid stream. The present invention utilizes the data acquired from its sensor readings of the sampler chamber's treated fluid reaction results, and produces control signals that control the chemical treatment of the main process fluid flow.

Another type of fluid control system that attempts to control the amount of chemical dosage required for treatment of a main fluid stream which is injected with a treatment fluid to cause a selected characteristic of the main fluid stream to match a desired level/set point or range is the Proportional Flow Controls Systems. These system types deliver a pre-calculated amount of treatment fluid that is proportionally based upon the amount of flow in the main fluid main stream. U.S. Pat. No. 6,346,198, discloses a system for controlling a rate at which a treatment fluid is introduced into a main stream to be treated so that a selected characteristic of the main stream matches a set point for the selected characteristic. U.S. Pat. No. 6,949,196 discloses a method and system for an improvement in the dosing of a chemical treatment in at least two locations along a side stream of a main flow of a liquid, and is based upon the proportional flow rate using a preset set point of chemical addition. Those previously mentioned prior art systems can not detect chemical-physical characteristic changes in the main fluid stream such as pH, conductivity, turbidity, and Total Suspended Solids, etc., and therefore since the amount of treatment fluid is calculated as a proportional value of the main stream flow the main flow chemical-physical characteristic changes pass unnoticed and undetected. The present invention is capable of detecting specifically those chemical-physical characteristic changes in the main flow stream and then responds by controlling the amount of treatment fluid based upon those changes detected.

U.S. Pat. No. 5,045,213 "Waste water treatment method and apparatus", discloses a system that ccontinuously removes precipitants and filters a sample flow of treated waste water subjected to pH level control and sensing the resulting turbidity after the filtering process as a control parameter, This system is designed for treating waste water for the removal of heavy metals. This method attempts to control the chemical dosage in a wastewater treatment process by sensing the turbidity. It can not offer a reliable turbidity measure since the system is inline and it doesn't provide time for the precipitation process to be completed. Other potential control problems exist with this method such as; the filtering process can get plugged and/or the filtration rate and mesh size used might not represent the real level of particulates removal and therefore can not offer a representative turbidity reading. Other patents offer different combinations of measurement and system setup, such as U.S. Pat. No. 6,949,196; U.S. Pat. No. 6,399,029; U.S. Pat. No. 4,170,553; U.S. Pat. No. 4,345, 996; U.S. Pat. No. 4,040,954. These patents present similar problems with their teachings, having limited capability of sensing turbidity adequately and accurately, thus having in-effective control of the chemical dosage method utilized.

Other attempts to achieve better fluid process control have been made using technologies as is used by "Streaming Current Detector" systems. This system is used in water treatment plants for coagulant and flocculent dosage control and has been in use for the past fifteen (15) years. However, the Streaming Current Detector technology has not overcome other industry challenges whereby the fluid stream's chemical characteristics present high fluctuations and thus narrowing its applications within water treatment industry. These characteristics can be further documented by the writings within the document "Streaming Current Instrument Training" written by Chuck Veal of Micrometrix Corp.

U.S. Pat. No. 6,515,481 "Streaming current detector with easily removable matched sleeve and piston set" disclosure the Streaming Current Detector with an attempt to improve the operational problems of this technology, which is not generally used in other fluid processing industries because this technology is affected by variations in fluid characteristics such as the fluid having a pH higher than 8, incremental changes in conductivity in the treatable fluid, along with incremental changes in suspended solids and debris present in the treatable fluid. It is known that industries like wastewater treatment, storm water treatment and industrial processes present those characteristic that limit the use of Streaming Current Detector as a controller.

The non-steady operation of the Streaming Current Detector has developed a reputation among Water Treatment Process operators for being more of an art than a science. The reasons for the reputation include the difficulty in detecting failure, the arbitrary nature of the measured units, inconsistence response with variations of pH, temperature, conductivity and suspended solids.

SUMMARY OF THE INVENTION

The system of the present invention precisely controls a treatment fluid delivery device so as to inject a correct amount of treatment fluid into a main fluid stream to cause a selected characteristic of the main fluid stream being processed to match a desired set point level. A sample of the main fluid stream solution is obtained at a location downstream from the treatment fluid injection site in the main fluid stream.

The sampled fluid stream solution is delivered to a sample reaction chamber wherein the sampled fluid solution is detained. The sampled fluid solution is detained for a predetermined period of time in order to allow its reactants to react and form the final processed product. The detention time provides an environment whereby the sampled fluid's final process results is comparable or equivalent to the final process results which occurs in the detention/reaction vessel of the main fluid solution flow, such as it would be at the effluent discharge of a clarifier. For that reason, the "activated complex" as is occurring during the delivery of the sampled fluid solution is a non-issue with the present invention, unlike as is with other anlysis and control technologies. The detained sampled fluid solution proceeds to emulate the process reactions of the main fluid stream. Within the sample reaction chamber is a sensor which analyzes the reaction results.

The sensor and its analyzer measures and records the level of the selected characteristic present in the detained sampled fluid. The analyzer measurement level as is recorded at a pre-determined period of sampled fluid solution's detention time, and the result of this analysis, is communicated to a controller which is utilized to control the treatment fluid delivery device which in turn delivers the treatment fluid to be injected the main fluid stream. If at the predetermined period during the sampled fluid solution's detention time, the fluid analyzer detects that its analysis of the most current characteristic of the detained sampled fluid solution is resulting in the residual characteristic being somewhat below the predetermined desired set point for the selected characteristic, the treatment fluid delivery device is adjusted to decrease the amount of treatment fluid injected into the main fluid stream. If at the predetermined period during the sampled fluid solution's detention time, the fluid analyzer detects that its analysis of the most current characteristic of the detained sampled fluid solution is resulting in the residual characteristic being somewhat above the predetermined desired set point for the selected characteristic, the treatment fluid delivery device is adjusted to increase the amount of treatment fluid injected into the main fluid stream.

When the analyzer detects a level of the selected characteristic matching the set point for the selected characteristic, or within the predetermined range of the set point, as desired by the operator, the present invention's controller maintains the rate of injection of the treatment fluid into the main fluid stream.

In all cases, when the controller sets the mode of treatment fluid feed rate as is derived from the sensor reading at the predetermined period of sampled fluid solution's detention time, that treatment fluid feed rate is continued until the following sensor reading at the predetermined period of sampled fluid solution's detention time, as is derived from within the same step of the following cycle of the present invention.

After the detained sampled fluid has been measured, analyzed, recorded and utilized by the controller to signal the treatment fluid delivery device its instructions, the detained sample fluid is replaced with newly sampled main fluid stream solution. The newly sampled fluid stream solution flows through the sample reaction chamber for a pre-determined period of time which flushes out any remaining residual characteristics of the just previously detained sampled fluid solution. At a pre-determined period of time, the newly sampled fluid stream solution is caused to be detained within the sample reaction chamber. This current volume of detained sampled fluid solution proceeds to emulate the processes of the main fluid stream as the injected treatment fluid interacts with the main fluid stream.

If the characteristics of the main fluid stream have changed, the most current processed sampled fluid stream will reflect this change. The sample reaction chamber sensor, analyzer and controller will send a signal instructing the treatment fluid delivery device to deliver the appropriate treatment fluid flow to be injected into the main fluid stream. Once the treatment fluid flow is adjusted and injected into the main fluid stream, its process results will match a desired set point level resulting in a selected characteristic of the treatment process of the main fluid stream.

The present invention's controller contains the logic for a continuous looped sequencing of the system steps of the invention, as described herein, that which provides for the ongoing treatment fluid flow adjustments as is required to correspond to the ongoing changes in the characteristics of the fluid within the main fluid stream.

A Feedback Verification analyzer can optionally be located downstream from the treatment fluid injector and at the main fluid stream effluent discharge to verify that the selected characteristic within the main fluid stream is at the desired set point. If the Feedback Verification Analyzer reading differs from the pre-established set point, above or below a certain pre-determined range of acceptability, the controller provides a warning notification which allows the operator to take notice of the difference between the data from the analyzer controller and the data from the Feedback Verification Analyzer, providing the information needed to determine as to whether adjustments are required so as to assure a reliable and efficient process operation. Data associated with settings for the treatment fluid delivery device and levels of selected characteristics within the main fluid stream at the end of the process being controlled can all be outputted relative to time for analysis by the operator to verify that the system is operating properly.

When the main fluid stream to be treated is a waste water or water stream and particulates within the waste water or water stream are to be removed, the treatment fluid used is typically a polymer containing compound or chemical such as ferric chloride. Within water or wastewater applications, the present invention controls the rate of chemical feed and can control the chemical preparation system known in the trade as a "Polymer Preparation Unit", which prepares the concentration level of polymer solution which is delivered to and injected into the main fluid stream. When utilizing the "Polymer Preparation Unit" control function, the present invention analyzes the data accumulated from its sensors and calculates and sends, at a predetermined interval, the proper signal instructions to the "Polymer Preparation Unit" for its formulation of the proper chemical concentration required to be delivered to the main fluid flow.

The present invention is applicable as well to those processes where a detention time is necessary in order to obtain reliable sensor readings, or where a chemical reaction in a process is not instantaneous. Examples of these processes can be found in water and wastewater treatment or industrial and commercial process applications where the selected characteristic to be measured and controlled could be the Free Hydrogen-ion Activity and/or the Total Dissolved Solids level, as well as other process controlling determinants.

The Arsenic Removal in a water treatment process is an example of where the present invention can be applied. Arsenic Removal systems use Ferric Chloride to lower the pH, providing the environment for Arsenic absorption and removal. To control the chemical dosage, as was in earlier plant designs, the pH sensor was placed after the mixing system, but this placement caused un-stable fluctuations in the pH sensor readings and made it complicated to provide a reliable control of the process since its control was based upon pH stabilization at a pre-determined set point. More recent designs of Arsenic Removal systems use the pH sensor readings taken at the end of the process filtration step for the purpose of monitoring and regulating the chemical dosage. With this configuration, the chemical dosage is controlled proportionally based upon the amount of influent flow to the system and the variant calculation derived from the analysis of the pH readings. The present invention, when used for controlling an Arsenic Removal system is capable of providing better control by utilizing its process emulation technique along with having a pH sensor affixed into the sample chamber of the present invention. By the present invention obtaining a sample of the most recently dosed and mixed main fluid flow, and detaining it within the sample chamber for a pre-determined period of time so as to emulate the reaction process of the Arsenic Removal system, the pH sensor can record the results and have its results utilized for a more rapid and stable controlling of the dosing requirements of the Arsenic Removal system.

There are other examples where the pH sensor utilized in the present invention can be implemented in the anelyzation process, substantially in those processes that are susceptible to high pH peaks or fluctuations in the acid/basic chemical addition, and/or where the time requirement for homogenization and complete chemical reactions are critical for accurate sensor readings. Industrial wastewater treatment processes used by paper mills, steel industries and electronic industries are some examples. Industrial processes such as is used in sugar cane factories are an example in industrial processes where the present invention utilizing a pH sensor can also be applied.

Other applications where the final result is subject to Total Dissolved Solids and conductivity measurement and regulation, the present invention can be a reliable and efficient control system with its using TDS and conductivity sensors.

The present invention can be located before the clarification means, obtaining of the process reaction results data from the present invention's process emulation and utilizing that data for controlling the process, rather than awaiting for a process result reading taken traditionally by a sensor placed after the discharge of the clarifier, thereby saving chemical usage along with making the process more efficient. Some additional applications can be found in storm water treatment and mining processes.

Alternately, when the system of the invention design requires faster correction responses delivered to the treatment fluid delivery device in order to compensate for the characteristic changes of the main fluid stream, additional sample fluid chambers and its sensors are installed and the programmed logic controller provides the continuous looped sequencing of the system steps of the invention to each of the sample fluid stream chambers in a pre-determined ladder stepped interval.

The present invention contains alarm notification and automated response capabilities whereby, through various output means, the process plant operator is notified that a component of the system of the present invention requires corrective measures. Some of the alarm notifications can be automatically acted upon, such as with the main fluid flow sensor indicating a no-flow status, the present invention would have the ability to shut down the chemical feed device along with the shutting down of some of the functionality of the present invention, until such time as to when the defect is noted to be corrected.

Some of the sensor interface and alarm capabilities of the present invention include sensor/analyzer malfunctions, high/low level indications along with flow indications, as an example.

OBJECTS OF THE INVENTION

Figure 1:
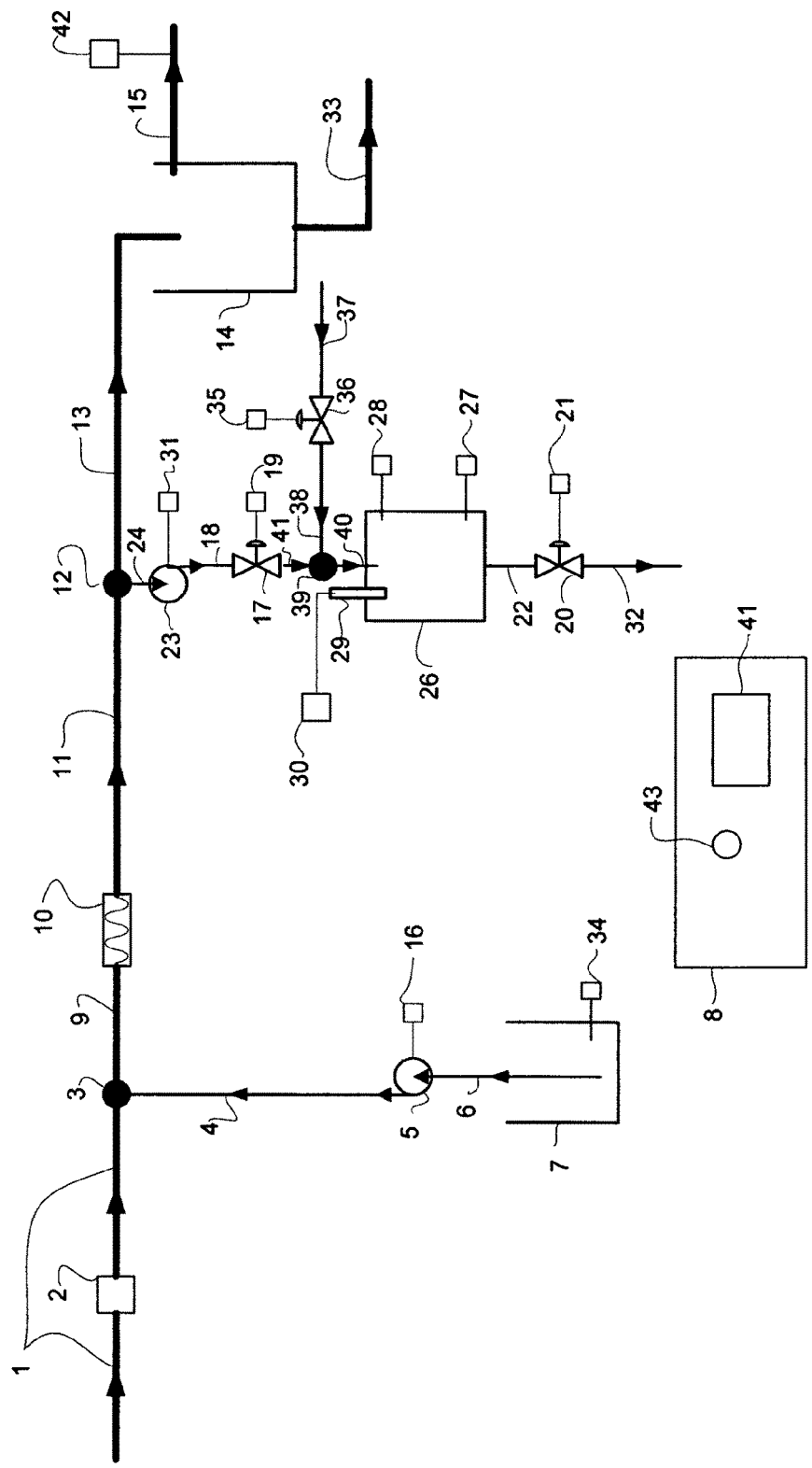
FIG. 1 is a schematic diagram illustrating the major components of the system of this invention as they would exist when incorporating the system of this invention into a water treatment system.

Accordingly, a primary object of the present invention is to provide a control system for adjusting a rate of introduction of treatment fluid into a main fluid stream which precisely causes a selected characteristic of the main fluid stream to match a set point for the selected characteristic.

Another object of the present invention is to provide a fluid treatment control system which minimizes an amount of treatment fluid required.

Another object of the present invention is to provide a control system for water treatment system which can reliably treat the water with a flocculating agent without over supplying or under supplying the flocculating agent into the water being treated.

Another object of the present invention is to provide a feedback signal to the Polymer Preparation System to control the polymer concentration to be injected into the main fluid stream.

Another object of the present invention is to provide a fluid feed control system which can operate with a minimum of operator monitoring and intervention.

Another object of the present invention is to provide a fluid treatment control system which can display and record data associated with analysis of selected characteristics of the fluid stream for review by an operator and can be utilized by a Programmable Logic Controller for delivering control signals to control devices.

Another object of the present invention is to provide a water treatment control system which utilizes turbidity sensing instrumentation and analyzers and to control a rate of introduction of flocculating agent into a water stream.

Another object of the present invention is to provide a wastewater treatment control system which utilizes pH, Total Dissolved Solids and conductivity sensing instrumentation and analyzers and to control a rate of introduction of at least one chemical reactant agent into a main fluid stream.

Another object of the present invention is to provide for a low chemical fluid level alarm indicating that the chemical tank fluid level is below a pre-selected operationally acceptable level initiated by a feedback signal derived from a level sensor installed in the chemical tank and delivered to the PLC for processing.

Another object of the present invention is to provide for a no-flow alarm indicating that the main stream flow is not being detected by a flow sensor installed in the main stream conduit with its feedback signal delivered to the PLC.

Another object of the present invention is to provide a sample chamber within which an emulation of the treatment process can be produced.

Another object of the present invention is to provide an environment as to where the "activated complex" of the treated solution is not a factor in obtaining accurate process data readings from sampled fluids.

Other further objects of the present invention will become apparent from a careful reading of the included drawing figures, the claims, specifications and detailed description of the invention.

THE PREFERRED EMBODIMENT

Within water, runoff water and wastewater fluid stream treatment processes, flocculation and precipitation procedures are utilized in order to remove unwanted particulates from the waters. The present invention uniquely addresses the monitoring and controlling of such procedures.

The preferred embodiment of the present invention describes its utilization in the treatment process of fluid streams of water types such as potable, runoff, wastewater, etc. for the removal of unwanted particulates contained within, such as suspended and dissolved solids. One method for analyzing and controlling the efficiency and results of the process as described within the preferred embodiment is the utilization of turbidity level monitoring. This embodiment as described herein utilizes the system and methods of the present invention and will serve as an example of how the present invention is used to uniquely control the flocculent agent solution feed into the treatable fluid stream and control the efficiency of the flocculation and precipitation treatment step of a fluid stream treatment process so that optimum levels of flocculation and precipitation treatments are obtained with minimum chemical usage.

A typical process step for the removal of unwanted suspended and dissolved solids from a fluid and/or a reduction of its turbidity is where a treatment chemical solution is added into the fluid stream and thus provides a conditioning of the resulting fluid stream solution wherein flocculation and the precipitation of unwanted particulates contained within the fluid stream solution can result. Types of treatment chemical solutions that could be used within a fluid stream processing step described as the preferred embodiment of the present invention are, but not limited to, treatment chemical solutions and process chemical combinations. The treatment chemical solution injected into the fluid stream is delivered by a chemical feed pump which delivers a measured quantity of treatment chemical solution to the fluid stream being treated. After the treatment chemical solution is injected into the fluid stream, the resulting fluid stream solution is mixed in order to achieve an even distribution of treatment chemical solution into the fluid stream.

The resulting fluid stream solution is delivered to a reaction/clarification apparatus or vessel wherein the velocity of the fluid stream solution is slowed and the flocculating and precipitation processes are performed. Therein the reaction/clarification apparatus or vessel, the flocculated particulates precipitate out of solution then are separated and removed from the reaction/clarification apparatus or vessel. The resulting clarified fluid stream, or effluent, is available for discharge or for further treatment(s) or use, depending upon pre-determined design specifications.

Typically, in the design and chemical specification phase, the fluid stream to be treated is sampled and scientifically tested for its reaction with varying types of treatment chemical solutions in order to determine the optimized formulation of the percentage of treatment chemical solution addition (as expressed by those familiar in the trade as Parts Per Million—PPM) into the processing step of flocculating and precipitating the particulates from of the art as "Jar Testing". The jar testing results can accurately provide the information relating to the selection process as to which treatment chemical solution to use in the process, but falls short in providing the accurate dosing formulation as it would be used in real time processing of the fluid stream wherein fluid characteristic variables occur. The dosing formulation that is represented by the results of jar testing provides the operator with only a starting point of the dosing requirement. As is in the process step of adding the treatment chemical solution at a specific feed rate to the fluid stream being treated, as variations in the consistency (the flow rate and or the percentage of unwanted particulates, solids and other variable components) of the fluid stream is encountered, these variables change the effectiveness of the treatment chemical solution's reaction with the fluid stream being treated. These variations with and within the fluid stream being treated need to be addressed by varying the feed rate and the volume of the treatment chemical solution that is injected into the fluid stream being treated in order to cause the desired reaction performance of this treatment process step so that the process operates in its optimum range of efficiency. The present invention addresses the controlling of treatment chemical solution dosing automatically and efficiently as the variations occur.

Figure 2:
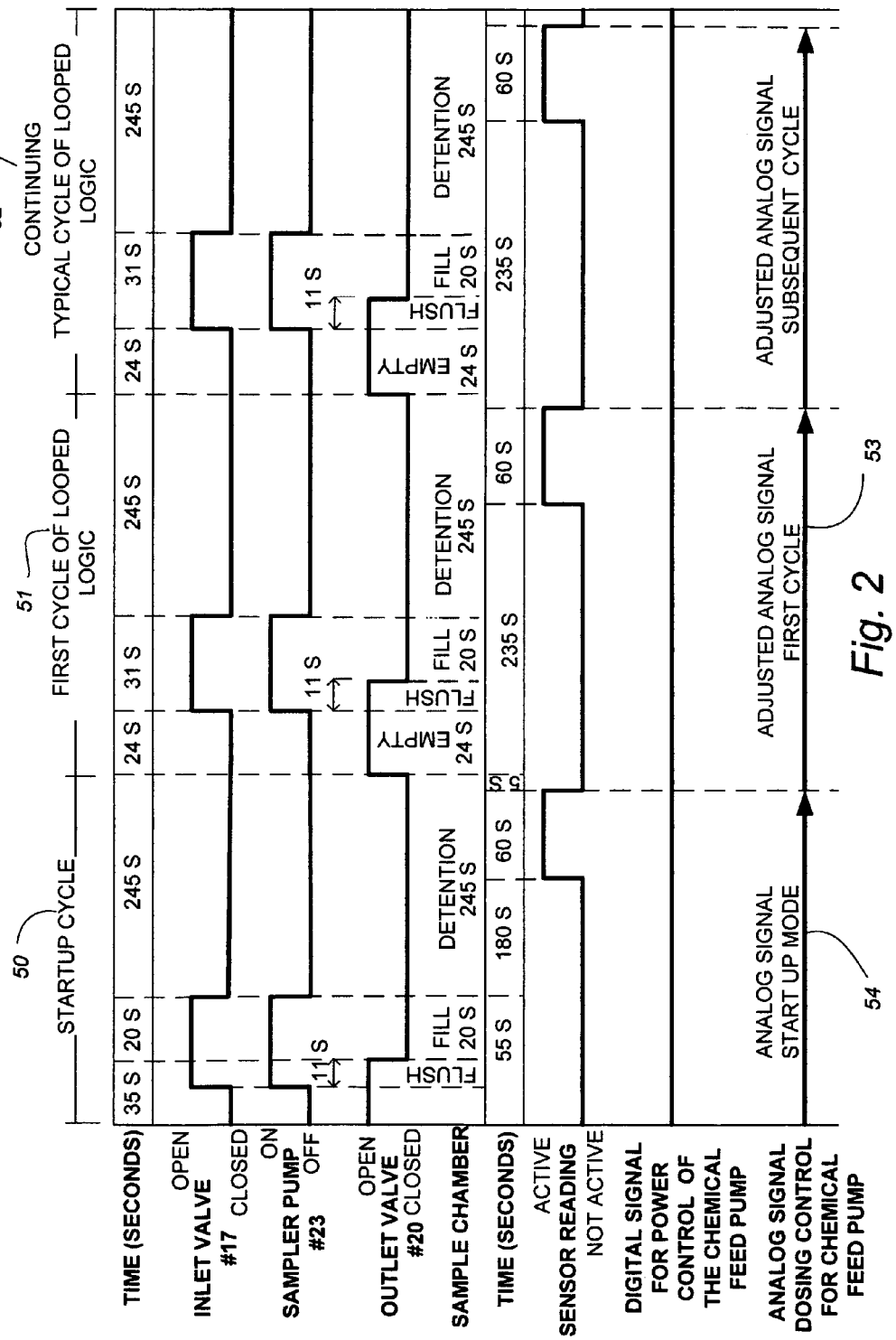
FIG. 2 is a schematic diagram illustrating a digital signal timing chart for operating of the preferred embodiment components of this invention.

The preferred embodiment of the present invention, as represented in FIG. 1, and FIG. 2 is a process step of a system used for treatment of a fluid stream such as water, runoff water or wastewater passing through a conduit (1), using analysis of characteristics of the diverted portion of the fluid stream. The system as described in this preferred embodiment of the present invention is used in the context of a water treatment system but is equally applicable to other fluid stream treatment systems where a treatment fluid is added to a main fluid stream, if desired, to exhibit a specified amount of a selected characteristic. Hence, this detailed description should not be construed as limiting this invention to merely water treatment systems.

In essence, with particular reference to FIG. 1, the basic details of the system of the present invention are described. A main conduit (1) having a fluid stream passing there through is treated in a controlled fashion according to the system of this invention. This process step as is herein described as the preferred embodiment is used for the removal of unwanted particulates contained within the fluid stream being treated. A flocculation and precipitation agent solution is utilized as the treatment chemical solution in this preferred embodiment. The process step of the preferred embodiment uses the present invention as a source for controlling the feed rate of treatment chemical solution into the main fluid stream. A chemical feed pump (5) injects a precisely measured amount of treatment chemical solution into the main fluid stream at injection point (3), that which controls, in turn, the reaction efficiency of the flocculation and precipitation process steps for the removal of unwanted suspended and dissolved solid particulates from the main fluid stream. The efficiency of the flocculating and precipitation process is measured in this preferred embodiment by the resulting turbidity residual as is measured by the sensor (29) of the present invention.

The process step of the preferred embodiment begins with its influent fluid stream being delivered through conduit (1) through a flow sensing device (2) and continuing there through to the treatment chemical solution injection point (3) wherein the fluid stream is injected with the treatment chemical solution being delivered through conduit (4) by way of chemical feed pump (5) which derives its chemical feed through conduit (6) from treatment chemical solution storage vessel (7). Chemical feed pump (5) is a variable feed chemical feed pump which is used to deliver the treatment chemical solution to the chemical treatment injection point (3) at a volumetric feed rate that is dictated by the programmable logic controller PLC (8). The resulting combined main fluid stream and treatment chemical solution are mixed using a mechanical or static mixer (10) which receives the main fluid stream solution flow through conduit (9) and continues through conduit (11) to sampling point intersection (12). As an alternate, a mixing station as well as any other conventional means used for mixing a treatment chemical solution into a main fluid stream being treated could be utilized via a conduit divergence at a point in conduit (9) substantially near and down stream of injection point (3). The mixing of the treatment chemical solution into the main fluid stream results in the main fluid stream and the treatment chemical solution forming a uniformly mixed fluid solution prior to the main fluid stream solution arriving at the point of sampling (12). The main fluid stream solution continues through conduit (13) and is delivered to reactor/clarification vessel (14) where the processes of flocculation and precipitation of particulates contained within the main fluid stream solution are accomplished.

The effluent, resulting from the process steps performed in the reactor/clarification vessel (14) is discharged through conduit (15) and delivered to a location pre-determined by the operator. The precipitated particulates which have been separated from the fluid solution flow within the reactor/clarification vessel are discharged via conduit (33) and delivered to a predetermined location for further handling.

At the point of sampling, sample pump (23) extracts a portion of the main fluid stream solution and delivers that extracted sampled portion of the main fluid stream solution flow through conduits (24) and (18), through inlet valve (17) and conduits (41) and (40) to and into sample reaction chamber (26). The sample reaction chamber (26) configured as having at least one inlet conduit (40) positioned substantially at the upper most interior portion of the sample reaction chamber (26) and as having at least one outlet conduit (22) positioned substantially at the most lowest interior portion of the sample reaction chamber (26). The sample reaction chamber (26) has installed within, a low level fluid sensor (27) located at the lower interior portion of at least one wall section of sample reaction chamber and a high level fluid sensor (28) located at the upper interior portion of at least one wall section of sample reaction chamber (26). Turbidity sensor element (29) is installed and positioned within the upper interior portion of the sample reaction chamber (26) so as to be submerged within substantially the upper portion of sampled main fluid stream solution detained within.

The PLC (8), preferably is in the form of at least one application specific integrated circuit, which is configured using known techniques to receive various different inputs identified herein as in the preferred embodiment of the present invention and to make adjustments to the system by sending various different outputs identified herein, controlling the process described herein as the preferred embodiment of the present invention in order to achieve results desired by the operator. The PLC (8) preferably and in addition to its ability to control devices associated with controlling processes, also delivers data to a display (41) and also an output system for printing onto paper or other media a hard copy for recording data indicative of the overall performance of the various different portions of the system.

The PLC (8) receives as input, the turbidity level value as a signal generated by the sensor (29) analyzer (30). The PLC (8) also receives signals from flow sensor (2) and treatment chemical solution storage vessel low level sensor (34), which is used to confirm operational state of the system's components. The PLC (8) also receives signals from the sample reaction chamber (26) low level and high level sensors (27) (28) at specific time frames during the operation of the present invention.

The PLC (8) additionally includes within its embedded logic data, a set point, as is typically provided by the operator, indicating the desired resulting level of residual turbidity within the main fluid stream after treatment. The set point can be a single set point or can be configured as an acceptable range or tolerance level above and below the single set point. Further, the PLC (8) can be programmed by the operator to control what information is represented on the display (41) and what information is recorded and outputted by data recorder/printer outputs provided by the PLC (8). Additionally and optionally, the PLC (8) has the capability for accepting and utilizing, as a process verifier and/or process adjuster in its embedded logic, additional data signals received from an analyzer and its sensor (42) located in the conduit (15) containing the effluent of the reactor/clarifier (14).

The PLC (8) has appropriate logic provided by the application specific integrated circuit, or other logic devices, such as software operating within a personal computer or other programmable computing device, which act upon the inputs provided by the operator and the signals received from the various different portions of the present invention used in its logic to generate various output signals.

As is in FIG. 2 Cycle Chart for PLC Logic which represents the preferred embodiment signal timing sequence for the PLC logic of the present invention and as is represented within the startup cycle (50), upon initializing the power up of the present invention as is in the preferred embodiment, the PLC (8) receives data from the flow sensor's controller (2) that there is flow of fluid within conduit (1) and from the treatment chemical solution storage vessel low level sensor (34) indicating there is at least sufficient quantity of treatment chemical solution contained within treatment chemical solution storage vessel (7) for delivery by chemical feed pump (5) to the point of injection into the main fluid stream (3). With confirmation of main fluid stream present in conduit (1) and confirmation of sufficient treatment chemical solution available in the treatment chemical solution storage vessel (7) the PLC (8), through its pre-determined embedded logic, proceeds with the methods of the present invention to control the optimization of the processing step of the main fluid stream as described herein as the preferred embodiment.

It should be noted that if the PLC (8) does not receive confirmation signals of operational status from either flow sensor (2) and/or treatment chemical solution storage vessel low level sensor (34), the PLC (8) initiates a warning alarm, preferably displayed on screen (41) and audibly delivered by a sound generating device such as a piezo buzzer (43) or the like, and does not proceed with its controlling procedures until such alarmed event is corrected and the proper operationally ready signals are able to be obtained form sensors (2) and (34).

Continuing with the startup cycle (50), the PLC (8), at substantially 0 seconds into the startup cycle (50), sends an analog signal to the chemical feed pump's controller (16) that instructs the chemical feed pump (5) to power up and continue to deliver from treatment chemical solution storage vessel (7) through conduits (6) and (4) treatment chemical solution at substantially its full dosing capability. At a predetermined period of approximately 5 seconds from initial startup, the PLC (8) sends to the chemical feed pump controller (16) analog signals which cause the chemical feed pump to linearly decrease its dosing flow rate, thereby decreasing the dosing feed of treatment chemical solution to the chemical injection point (3) where the flow of treatment chemical solution is injected into the main fluid stream within conduit (1). The PLC (8) delivers the dosing decrease analog signals to the chemical feed pump controller (16) for approximately 290 seconds or at least until the pre-determined set point signal, as is embedded into the PLC logic, is attained. The chemical feed pump (5) thereafter continues to deliver treatment chemical solution to the chemical injection point (3) where the treatment chemical solution flow is injected into the main fluid stream within conduit (1). The resulting main fluid solution flow is delivered through conduit (9) to and through static mixer (10) and conduit (11) to and through sampling zone (12) and further travels through conduit (13) to main fluid solution flow reactor/clarification zone (14) where substantially all of the flocculation and precipitation reactions and processes for separation of unwanted particulates from the main fluid solution flow occurs.

At approximately 24 seconds from initiation of start up cycle (50), the PLC (8) delivers command signals to sample reaction chamber outlet valve relay/controller (21) and inlet valve relay/controller (19) to cause valves (20) and (17) to open. Substantially at the same time, PLC (8) signals relay/controller (31) to power up sampling pump (23) to cause a sampled flow of the main fluid solution flow to be delivered from sampling zone (12) through conduits (24) and (18), continuing through valve (17), conduit (41), junction point (39), conduit (40) into and through sample reaction chamber (26), through conduit (22), valve (20) and discharged through conduit (32). The previously described activities of the present invention initiated at approximately 24 seconds from initiation of start up cycle (50) provides for a flushing of the sample reaction chamber (26) of its residual particulates and the like, in preparation for the volume of sampled flow of the main fluid solution flow from sampling zone (12) that will be caused to be detained for testing. This flushing step prepares the sample reaction chamber (26) for the next step of the present invention which is the filling of the sample reaction chamber with the most current sampling of main fluid solution flow as is in conduit (11) derived at sampling point (12).

At approximately 35 seconds from initiation of start up, PLC (8) delivers signal to relay/controller (21) to close valve (20), causing sample reaction chamber (26) to fill with most recently sampled main fluid solution flow. The closing of valve (20) causes the sampled main fluid solution flow to be detained and fill the sample reaction chamber (26). At least one low level fluid sensor (27) is located substantially at the lower portion of and preferably within the interior of sample reaction chamber (26) positioned so as to be able to confirm the presence of at least a substantial existence of a minimal quantity of sampled main fluid solution flow being contained within said sample reaction chamber (26), along with at least one high level sensor (28) preferably located substantially at the upper portion and within the interior of the sample reaction chamber (26) positioned so as to sense the availability of a pre-determined volume of sampled main fluid solution flow as would be contained within said sample reaction chamber (26). Upon sensors (27) verifying by sending a signal to PLC (8) that at least the minimum level of sampled main fluid solution flow has been attained within said sample reaction chamber (26), and sensor (28) signaling the PLC (8) that the correct level of sampled main fluid solution flow is contained within said sample reaction chamber (26), the PLC (8) then causes the sampled main fluid solution flow to cease by conveying command signals, substantially all at the same time, to the controller (31) of pump (23) to stop pumping, and to relay/controller (19) to close valve (17). The previously described activities of the present invention initiated at approximately 35 seconds from initiation of start up cycle (50) provides for the capturing of the most recently sampled main fluid solution flow and the start of its detention period so as to provide the environment within sample reaction chamber (26) for the desired reaction between the chemical treatment solution fluid as was injected into the main fluid stream as sampled at sample zone (12) and the unwanted particulates contained within the sampled main fluid solution.

The present invention utilizes at least one turbidity sensing device (29) with at least one turbidity sensing element securely positioned in the interior and substantially at the upper portion and of said sample reaction chamber (26) and at a pre-determined depth into sample reaction chamber whereas the sensing element portion is located below and substantially into the uppermost portion of the volume of detained sampled main fluid solution. The volume of sampled main flow fluid solution as contained within sample reaction chamber (26) is determined and controlled by confirming signal from high level sensor (28) contained within said sample reaction chamber (26) as is sent to the PLC (8) which dictates the maximum volume of sampled main fluid solution to be contained within sample reaction chamber (26) by then sending control signals that which causes the sample feed pump (23) to stop and inlet valve (17) to close, thus limiting the volume of sampled main fluid solution being delivered into sample reaction chamber (26) by and according to the positioning of the high level sensor (28). The sample reaction chamber fill step is completed.

The sampled main fluid solution residing within sample reaction chamber (26) is detained for approximately 245 additional seconds wherein the desired reactions occur. At approximately 180 seconds from the initiation of the detainment step, and for approximately 60 seconds thereafter, the PLC (8) records data signals received from analyzer (30), that which was obtained from sensing device (29). These data signals are processed by the embedded logic of the PLC (8) that which derives a sequence of signal instructions that are delivered to the chemical feed pump flow rate controller (16) to adjust the chemical feed pump (5) treatment chemical solution feed rate, according to the results of the calculations computed and instructions derived from the pre-determined logic installed within PLC (8). The steps of analyzing of the sampled main stream fluid flow reaction process and the chemical feed pump feed rate adjustment process are initiated.

The sampled fluid solution flow that is contained within sample reaction chamber (26) which was obtained at sampling point (12) from the main fluid solution flow being treated, has substantially the same characteristics as does the fluid solution flow that is being delivered to clarification vessel (14) via conduit (13). Within the reactor/clarification vessel (14), the main fluid solution flow undergoes reactions that are substantially flocculation and precipitation processes. As is within the present invention, the sampled fluid solution flow retained and detained within the sample reaction chamber (26) undergoes reactions which are substantially flocculation and precipitation processes. Within substantially the upper portion of the detained volume of sampled main fluid solution flow, the desired results of the reaction processes of flocculation and precipitation are made more rapidly evident than would be if having to await for the desired reactions to occur to the entire volume of the detained sampled main fluid solution as is contained within the sample reaction chamber (26). The upper portion of the detained sampled main fluid solution flow as is described previously and as is tested and from which data is derived by the sensor (29) at predetermined periods of time into the detention period, is the portion of the detained sampled main fluid stream solution that is utilized by the present invention to be representative of the resulting characteristic state of the reactions occurring within the entire volume of detained sampled main fluid solution stream. Thus, it becomes obvious that the resulting characteristics and derived data from the resulting reactions within the sampled main fluid solution stream being processed within said sample reaction chamber (26) are available quicker than that be of the resulting effluent characteristics attained from the main fluid solution stream being processed as is in the reactor/clarification vessel (14). The upper portion of the sampled fluid solution stream, after processing, substantially emulates the characteristics of effluent as is derived from the main fluid solution stream after being processed within reactor/clarification vessel (14) and as being discharged as effluent within conduit (15). The primary reasons for the resulting emulated effluent portion of the sample reaction chamber (26) attaining precipitation and clarification faster than the resulting effluent of the clarification vessel (14) is due in part to; a) flocculation and precipitation of particulates occur faster within a still body of water as is in the sample reaction chamber of the present invention, as compared with the length of time it takes to perform the flocculation and precipitation processes within that of a moving body of water as is typically found with traditional clarification processes, b) the volumetric scale differential between the approximately one gallon capacity sizing of the sample reaction chamber and the many thousands of gallons capacities of typical clarification vessels, c) the ability to locate the sensor's sensing element submerged in the sampled main fluid solution detained within the sample reaction chamber and substantially within the depth range of the early stage of emulated effluent development derived from that of the reaction processes substantially being the flocculation and precipitation processes occurring in the sample reaction chamber, as opposed to the location of the sensor typically located within the effluent stream contained within conduit (15) of clarifier/reactor (14). d) Consequently, the turbidity readings in the sample reaction chamber occurs in real time, rather than traditional methods where the turbidity reading is obtained in a delayed format described by the formula Time Differential=Clarifier Volume/Flow (gpm). e) As a result, the PID loop for testing the resulting emulated effluent contained within the sample reaction chamber is stable, constant and responds to errors based on near real time results.

To represent the efficiencies obtained in controlling a process as described in the preferred embodiment with the use of the present invention, assume the treatment process as described has a main fluid stream solution flow of 100 gpm and a processing time requirement of 30 minutes from the treatment fluid injection point (3) to the effluent discharge conduit (15) of the reactor/clarification vessel (14). Variations of the quality of incoming main fluid stream as delivered in conduit (1) to the process step is expected and it is for that reason for efficient control of the feed rate of the treatment fluid injection into the main fluid stream is required.

It can be calculated that a total of 3,000 gallons of main fluid solution flow has been treated (from (3) to (15)) prior to obtaining data derived from the resulting reaction of such treatment and utilizing that data in controlling the feed flow of the treatment fluid solution used in the process. If one were to utilize the present invention, as represented in FIG. 2 (52), and using the same 100 gpm main fluid solution flow, the total time that a complete testing cycle for obtaining the resulting characteristics of an emulated effluent is 300 seconds (53) or 5 minutes which then calculates to a total of 500 gallons of main fluid solution flow being treated prior to obtaining data derived from the resulting reaction of such treatment. Data derived from the utilization of the present invention with its 5 minute looped testing cycle (52) is made more readily available that which is used to control the feed flow of the treatment fluid solution for the process of the preferred embodiment described herein than would an approximate 30 minute delay as found in traditional reactor/clarification processes. Less chemical treatment fluid solution is required because, as demonstrated in this example, only 500 gallons of main fluid solution flow passes the treatment fluid solution injection point (3) until the next adjustment in the feed of treatment fluid solution occurs as compared with 2,500 gallons of is main fluid solution flow passes the treatment fluid solution injection point (3) until the next adjustment in the feed of treatment fluid solution occurs with traditional reactor/clarification processes. A more efficient process control is achieved with using the present invention, thus saving chemical costs and having less error fluctuations in the effluent quality than traditional means.

The reactions referred to as is in both the clarifier (14) and the sample reaction chamber (26) are the flocculation and precipitation reaction processes of the preferred embodiment as described herein that which are utilized for the removal of unwanted suspended and dissolved particulates from each of its contained main fluid solution. The sampled fluid solution flow delivered to sample reaction chamber (26) is detained for approximately 5 minutes, as is in this preferred embodiment, in order to permit the reaction of flocculation and precipitation of a portion of its unwanted suspended and dissolved particulates to occur. The reaction results occurring within the sample reaction chamber (26) are monitored for its residual turbidity level by a turbidity sensing instrument (29) of the type such as one manufactured by HACH, model sc100/LXV423.99.10100 SOLITAX t-line sc/immersion probe, as is used in this preferred embodiment. The turbidity sensing instrument's sensing element is positioned within the interior wall sections of the sample reaction chamber (26) and within the detained sampled fluid stream solution flow whereas it is, after the approximately 5 minute detainment of the sampled fluid stream solution flow wherein the flocculation and precipitation reactions having occurred and whereas the sensing of the portion of the resulting sampled fluid stream solution flow portion that was pre-determined to best represent the effluent quality derived from clarifier (14) as would occur with the fluid solution flow as was sampled at sample point (12). As is with the present invention, the turbidity sensor (29) sends signals to its analyzer (30) which converts the signals to a data stream recognizable by the PLC (8) which utilizes that data in its pre-determined program logic for calculating the error corrections needed for the signals it generates which give instructions to the process control devices that control the system of the present invention and the controllable processes performed as is in the preferred embodiment.

At approximately 295 seconds from startup, which corresponds to the end of the 60 second detainment process, the PLC (8) ceases to accept new signals from Analyzer (30) and proceeds to deliver continuously to the Chemical Feed Pump Flow Rate controller (16) an analog signal corresponding to the most recent control signal as was generated by the contained logic of PLC (8) replacing the pre-existing start-up analog signal value.

Analyzing the reaction progress and Chemical Feed Pump Flow Rate Adjustment process of the startup cycle is ended The PLC (8) continues to send to the Chemical Feed Pump Flow Rate controller (16) the control signal as is the same as was determined by the embedded logic contained within PLC (8) as was at the end of the Chemical Feed Pump Flow Rate Adjustment process step. This process step determined the fixed feed rate of the chemical feed pump (5) as is continued for a period of approximately 230 additional seconds at which time the Analyzer (30) for Sensor (29) proceeds to deliver to PLC (8) the reaction progress of the sample fluid contained within the sample reaction chamber (26) and Chemical Feed Pump Flow Rate Adjustment step is initiated in the immediately following PLC (8) looped logic control cycle noted as in FIG. 2 as first cycle of looped logic (51).

The First Cycle of the PLC Looped Logic (51) is initiated. All cycles of the present invention that follow the First Cycle of the PLC Looped Logic (51), as noted in FIG. 2 as Continuing Typical Cycle of Looped Logic (52) will be typical in operational processes as in the First Cycle of PLC Looped Logic (51).

The Startup Cycle (50) of the present invention is completed at approximately 5 seconds after the PLC (8) initiates the delivery of it's most current fixed treatment chemical solution feed rate instruction signal to the treatment chemical solution feed pump feed rate controller (16).

The process of the First Cycle of the PLC Looped Logic (51) is initiated. PLC (8) delivers a signal to Outlet Valve (20) controller (21) to open, thus causing the sampled main fluid stream solution that was detained within the sample reaction chamber (26) to be discharged, thus emptying Sample Reaction Chamber (26).

At approximately 24 seconds from initiation of the present cycle the PLC (8) sends control signals to relay/controller (31) to cause sampling pump (23) to operate, and to controller (19) of inlet valve (17) to open. The flush process is initiated.

At approximately 35 seconds from initiation of initiation of the present cycle, PLC (8) sends control signal to controller (21) for outlet valve (20) to close. The flush process is terminated and the fill process is initiated and operational for approximately 20 additional seconds or until the PLC (8) receives a signal from High Level sensor (28) which indicates that fluid in Sample Reaction Chamber (26) has achieved the desired pre-set level. During the fill process, the Low Level sensor (27) sends signal to PLC indicating Fill process is operational. If no signal from the low level sensor (27) was received by PLC (8), alarm indicator on the display (41) and alarm buzzer (43) will sound and the operation of present invention will terminate until system problem is corrected and the present invention is reset by operator.

At approximately 55 seconds from initiation of current cycle; or upon PLC (8) receiving signal from High Level sensor (28) indicating that fluid in Sample Reaction Chamber (26) has achieved the desired pre-set level, the PLC (8) sends control signals to relay/controller (31) for sampling pump (23) to stop pumping, and to controller (19) for inlet valve (17) to close. The detention process of the currently sampled main fluid stream detained within the sample reaction chamber (26) is initiated At approximately 235 seconds from initiation of current cycle, and for approximately 60 additional seconds, PLC (8) utilizes received signals from Analyzer (30) for Sensor (29) and proceeds to deliver to Chemical Feed Pump Flow Rate controller (16), signals that which adjusts the flocculent agent solution feed rate linearly and according to the results of the pre-determined logic installed within PLC (8).

The analyzing of the reaction progress of the sampled main fluid stream within the sample reaction chamber and Chemical Feed Pump Flow Rate Adjustment steps are initiated At approximately 295 seconds from initiation of current cycle the PLC (8) ceases to accept new signals from Analyzer #30 and proceeds to deliver continuously to the Chemical Feed Pump Flow Rate controller (16) which controls the feed rate of chemical feed pump (5) an analog signal corresponding to its most recent control signal as generated by the PLC (8) and its contained logic.

The analyzing of the reaction progress and the calculations performed by the embedded logic of the PLC (8) that which adjusted the Chemical Feed Pump Flow Rate is terminated.

The PLC (8), for a period of approximately 235 additional seconds, continues to send to the Chemical Feed Pump (5) the control signal as is the same signal as was determined by the embedded logic of PLC (8) at the end of the Chemical Feed Pump Adjustment process.

The next Cycle of the PLC Looped Logic is initiated. All cycles that follow are typical in instruction from the PLC as was described herein as the First Cycle of Looped Logic (51).

The present invention proceeds to repeat its steps automatically in sequential order, as was previously described herein, that which provides for the process step of the preferred embodiment to be controlled by the steps of the present invention ongoing.

The present invention provides for, as an alternate for this preferred embodiment, the utilization of multiple sensing device configurations placed within the sample reaction chamber (26), and within multiple sample reaction chambers.

The present invention provides for, as an alternate for this preferred embodiment, a programming alternate which incorporates program control of the timing length of the detention step so as to limit the detention time needed for that cycle as would be calculated from the sensor reading differentials which occur during a predetermined time segment of that detention step. As an example, within any 10 second segment of the detention step, if the rate of change of the sensor readings are less than 2% from the start of that 10 second segment, then the detention step would be caused to end and the data point sent to the PLC (8) at that time would be used as a part of the calculation sequence of the PLC (8) embedded logic to set the feed rate of the chemical feed pump (5) for the following cycle.

The present invention provides for, as an alternate for this preferred embodiment, a programming alternate which would control the chemical feed rate so as to adapt the treatment steps to extreme characteristic fluctuations of the main fluid stream which when indicative of characteristics that are beyond the predetermined acceptability ranges established for the process step, the chemical feed rate will be adjusted so as to limit the overfeeding or underfeeding of chemicals. This alternate would offer the operator better control under extreme and extraordinary conditions.

The present invention provides for, as an alternate for this preferred embodiment, multiple reaction chambers sequentially staged in a ladder configuration for main fluid stream processes which require faster treatment chemical solution adjustment responses than which can be obtained with a single sample reaction chamber configuration. This alternate would be beneficial, as an example, when the detainment time required for the sample fluid stream to perform its desired reaction to a point of completion is determined to be excessive for the efficient control of the processing of the main fluid stream and whereas the present invention is not able to sense the results of the reaction that would reflect the preferred embodiment process effluent design characteristics so as to attain the acceptable process control parameters sought after.

The present invention as indicated in FIG. 1 has a means for providing an alternate fluid feed source to the sample reaction chamber (26) via conduit (37), through control valve (36), conduits (39) and (40). This alternate fluid feed configuration can be utilized for providing a flushing agent for cleaning the chamber, providing a sample feed from the clarifier/reaction vessel effluent for purpose of analysis, or to be utilized for any other reason that the operator may so desire.

The present invention, as is described in the preferred embodiment, can be represented alternately as a batch fluid treatment process as would be utilized with batch treatment steps performed for each of the steps as is described in the preferred embodiment. The alternate as described herein could be represented by a batch of treatable fluid which is fed into a vessel wherein the chemical treatment solution is delivered, mixed into and thus reacts with the batch of treatable fluid solution. As exampled by utilizing a single process vessel, and within that vessel, the flocculation and precipitation processing of the unwanted particulates contained within the fluid solution are performed. The resulting fluid effluent and the separated particulates are each separately removed from the vessel and the process as described herein is repeated, as might be required.

This disclosure is provided to reveal a preferred embodiment of the invention and the best mode for practicing the invention. It should be apparent that various different modifications can be made to the preferred embodiment without departing from the scope and spirit of this disclosure. Various additional fluid characteristics such as temperature, pH, color, conductivity, viscosity, etc., can be monitored and controlled when using the present invention. When structures are identified as a means to perform a function, the identification is intended to include all structures which can perform the function specified.

What is claimed is:

1. A method for monitoring at least one characteristic of a fluid flowing in a main fluid stream, and controlling the at least one monitored characteristic of the fluid flowing in the main fluid stream to a desired level by treatment of the fluid flowing in the main fluid stream with at least one treatment fluid added to the main fluid stream, the method comprising:
adding at least one treatment fluid to the fluid flowing in the main fluid stream;

delivering the fluid flowing in the main fluid stream and the at least one added treatment fluid through a conduit to a reactor/clarification vessel wherein the treatment of the main fluid by the at least one treatment fluid is accomplished such that the at least one monitored characteristic reaches the desired level;

a diverting step consisting of diverting a sample fluid stream from the treatment fluid added main fluid stream in the conduit at a diversion point downstream of an adding point of the at least one treatment fluid to the fluid flowing in the main fluid stream, and upstream of any reactor/clarification vessel which treats the fluid flowing in the main fluid stream with the added treatment fluid, wherein the sample fluid stream diverted from the treatment fluid added main fluid stream is volumetrically smaller than the main fluid stream, and the reaction conditions of the sample fluid stream emulate the reaction conditions in the main fluid stream;

a detaining step consisting of detaining the sample fluid stream diverted from the treatment fluid added main fluid stream in the conduit for a predetermined detainment period of time in at least one detainment area separate from and independent of the reactor/clarification vessel so as to allow the fluid flowing in the main fluid stream and the added at least one treatment fluid to react in the detainment area;

wherein the detainment period of time of the sample fluid stream diverted from the treatment fluid added main fluid stream in the conduit is set to be such that reaction conditions at a given time based on the volume of the detained sample fluid stream correspond to reaction conditions at a future time based on the larger volume in the reactor/clarification vessel;

analyzing at least a portion of the detained sample fluid stream diverted from the treatment fluid added main fluid stream in the conduit during the predetermined detainment period to determine whether said at least one characteristic of the analyzed portion of the detained sample fluid stream is at the desired level; and controlling a rate of adding the at least one treatment fluid added to the fluid flowing in the main fluid stream, based on the results of the analysis of the at least a portion of the detained sample fluid stream diverted from the treatment fluid added main fluid stream in the conduit during the predetermined detainment period, such that controlling said rate of adding causes the at least one monitored characteristic of the fluid in the reactor/clarification vessel to be at the desired level at at least one predetermined time.

2. The method according to claim 1, wherein, the adding point of the at least one treatment fluid to the fluid flowing in the main fluid stream, and the downstream diversion point of the sample fluid stream, are spaced apart to allow mixing of the fluid flowing in the main fluid stream and the at least one treatment fluid, such that the diverted sample fluid stream comprises mixed fluids.

3. The method according to claim 1, wherein the at least a portion of the detained sample fluid stream is analyzed for the at least one monitored characteristic during the predetermined detainment period.

4. The method according to claim 3, wherein the analysis of the at least one monitored characteristic of the detained sample fluid determines whether the at least one monitored characteristic corresponds to a desired level.

5. The method according to claim 4, wherein, when the at least one monitored characteristic of the detained sample fluid corresponds to the desired level, the rate of adding the at least one treatment fluid added to the fluid flowing in the main fluid stream is maintained.

6. The method according to claim 4, wherein, when the at least one monitored characteristic of the detained sample fluid does not correspond to the desired level, the rate of adding the at least one treatment fluid added to the fluid flowing in the main fluid stream is adjusted.

7. The method according to claim 6, wherein, the rate of adding the at least one treatment fluid added to the fluid flowing in the main fluid stream is adjusted by adjusting a flow rate of the addition of the treatment fluid.

8. The method according to claim 7, wherein adjusting the flow of the at least one treatment fluid added to the fluid flowing in the main fluid stream, further comprises at least one repeat of:

the diversion step of the sample fluid stream diverted from the treatment fluid added main fluid stream in the conduit;

the detainment step of the sample fluid stream diverted from the treatment fluid added main fluid stream in the conduit; and the analysis step of the at least a portion of the detained sample fluid stream diverted from the treatment fluid added main fluid stream in the conduit.

9. The method according to claim 7, wherein adjusting the flow of the at least one treatment fluid added to the fluid flowing in the main fluid stream is repeated until the at least one monitored characteristic of the detained sample fluid corresponds to the desired level.

10. The method according to claim 6, wherein, the rate of adding the at least one treatment fluid added to the fluid flowing in the main fluid stream is adjusted by adjusting a dilution rate of a treatment fluid concentrate in a preparation of the at least one treatment fluid.

11. The method according to claim 10, wherein the adjusting the flow of the at least one treatment fluid added to the fluid flowing in the main fluid stream, further comprises at least one repeat of:

the diversion step of the sample fluid stream diverted from the treatment fluid added main fluid stream in the conduit;

the detainment step of the sample fluid stream diverted from the treatment fluid added main fluid stream in the conduit; and the analysis step of the at least a portion of the detained sample fluid stream diverted from the treatment fluid added main fluid stream in the conduit.

12. The method according to claim 10, wherein adjusting the flow of the at least one treatment fluid added to the fluid flowing in the main fluid stream is repeated until the at least one monitored characteristic of the detained sample fluid corresponds to the desired level.

13. The method according to claim 1, wherein, when the at least one monitored characteristic of the detained sample fluid corresponds to the desired level, maintenance of the rate of adding the at least one treatment fluid added to the fluid flowing in the main fluid stream further comprises repeated cycles of:

the diversion step of the sample fluid stream diverted from the treatment fluid added main fluid stream in the conduit;

the detainment step of the sample fluid stream diverted from the treatment fluid added main fluid stream in the conduit; and the analysis step of the at least a portion of the detained sample fluid stream diverted from the treatment fluid added main fluid stream in the conduit, at predetermined times so as to continuously maintain the at least one monitored characteristic of the detained sample fluid to correspond to the desired level.

14. The method according to claim 3, wherein the at least a portion of the detained sample fluid stream is first analyzed at a predetermined time in the detainment period, such that a first time of analysis is before a time required for a reaction in the reactor/clarification vessel between the fluid flowing in the main fluid stream and the at least one added treatment fluid to reach completion.

15. The method according to claim 14, wherein said reaction in said reactor/clarification vessel causes a change in the at least one monitored characteristic of the fluid flowing in the main fluid stream.

16. The method according to claim 1, wherein the desired level of the at least one monitored characteristic of the fluid flowing the in main fluid stream corresponds to at least one value within a predetermined desired range.

17. The method according to claim 1, wherein the at least one monitored characteristic of the fluid flowing in the main fluid stream includes an amount of particulates contained in the main fluid flowing in the main fluid stream, and the treatment fluid includes a flocculent containing compound capable of adhering and/or reacting to the particulates contained in the main fluid flowing in the main fluid stream.

* * * * *